United States Patent

Pacetti et al.

(10) Patent No.: US 7,985,440 B2
(45) Date of Patent: Jul. 26, 2011

(54) METHOD OF USING A MANDREL TO COAT A STENT

(75) Inventors: Stephen D. Pacetti, San Jose, CA (US); Mohammed E. Moein, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 455 days.

(21) Appl. No.: 11/222,053

(22) Filed: Sep. 7, 2005

(65) Prior Publication Data

US 2006/0035012 A1 Feb. 16, 2006

Related U.S. Application Data

(62) Division of application No. 10/678,979, filed on Oct. 2, 2003, now Pat. No. 6,955,723, which is a division of application No. 09/894,248, filed on Jun. 27, 2001, now Pat. No. 6,695,920.

(51) Int. Cl.
*B05D 5/00* (2006.01)
*B05D 1/02* (2006.01)
*B05B 13/04* (2006.01)
*B05C 1/00* (2006.01)
*A61L 33/00* (2006.01)

(52) U.S. Cl. .... 427/2.1; 427/2.24; 427/2.25; 427/421.1; 427/425; 118/320; 118/232

(58) Field of Classification Search ................ 427/2.24, 427/2.25, 2.28, 2.1, 421.1, 425; 118/320, 118/232

See application file for complete search history.

(56) References Cited

U.S. PATENT DOCUMENTS

| | | | |
|---|---|---|---|
| 2,072,303 A | 3/1937 | Hermann et al. | |
| 2,386,454 A | 10/1945 | Frosch et al. | |
| 2,845,346 A | 7/1958 | Scanlon et al. | |
| 3,016,875 A | 1/1962 | Ballentine, Jr. et al. | |
| 3,773,737 A | 11/1973 | Goodman et al. | |
| 3,827,139 A | 8/1974 | Norteman | |
| 3,849,514 A | 11/1974 | Gray, Jr. et al. | |
| 3,882,816 A | 5/1975 | Rooz et al. | |
| 3,995,075 A | 11/1976 | Cernauskas et al. | |
| 4,011,388 A | 3/1977 | Murphy et al. | |
| 4,082,212 A | 4/1978 | Headrick et al. | |
| 4,201,149 A | 5/1980 | Koester et al. | |
| 4,226,243 A | 10/1980 | Shalaby et al. | |
| 4,269,713 A | 5/1981 | Yamashita et al. | |
| 4,290,383 A | 9/1981 | Pfender | |

(Continued)

FOREIGN PATENT DOCUMENTS

DE    42 24 401    1/1994

(Continued)

OTHER PUBLICATIONS 780S series Spray Valves Valvenate 7040 Controller Operating Manual, EFD company (2002).*

(Continued)

*Primary Examiner* — Timothy H Meeks
*Assistant Examiner* — Cachet I Sellman
(74) *Attorney, Agent, or Firm* — Squire Sanders Dempsey, (US) LLP (57) ABSTRACT

A method of applying a coating to a stent supported by a mandrel is disclosed.

39 Claims, 2 Drawing Sheets

U.S. PATENT DOCUMENTS

| | | |
|---|---|---|
| 4,329,383 A | 5/1982 | Joh |
| 4,343,931 A | 8/1982 | Barrows |
| 4,459,252 A | 7/1984 | MacGregor |
| 4,489,670 A | 12/1984 | Mosser et al. |
| 4,529,792 A | 7/1985 | Barrows |
| 4,560,374 A | 12/1985 | Hammerslag |
| 4,611,051 A | 9/1986 | Hayes et al. |
| 4,616,593 A | 10/1986 | Kawamura et al. |
| 4,629,563 A | 12/1986 | Wrasidlo |
| 4,640,846 A | 2/1987 | Kuo |
| 4,656,242 A | 4/1987 | Swan et al. |
| 4,733,665 A | 3/1988 | Palmaz |
| 4,762,128 A | 8/1988 | Rosenbluth |
| 4,798,585 A | 1/1989 | Inoue et al. |
| 4,800,882 A | 1/1989 | Gianturco |
| 4,822,535 A | 4/1989 | Ekman et al. |
| 4,839,055 A | 6/1989 | Ishizaki et al. |
| 4,846,791 A | 7/1989 | Hattler et al. |
| 4,865,879 A | 9/1989 | Finlay |
| 4,882,168 A | 11/1989 | Casey et al. |
| 4,886,062 A | 12/1989 | Wiktor |
| 4,893,623 A | 1/1990 | Rosenbluth |
| 4,906,423 A | 3/1990 | Frisch |
| 4,931,287 A | 6/1990 | Bae et al. |
| 4,941,870 A | 7/1990 | Okada et al. |
| 4,955,899 A | 9/1990 | Della Corna et al. |
| 4,976,736 A | 12/1990 | White et al. |
| 4,977,901 A | 12/1990 | Ofstead |
| 4,992,312 A | 2/1991 | Frisch |
| 5,017,420 A | 5/1991 | Marikar |
| 5,019,096 A | 5/1991 | Fox, Jr. et al. |
| 5,033,405 A | 7/1991 | Yamada et al. |
| 5,037,392 A | 8/1991 | Hillstead |
| 5,037,427 A | 8/1991 | Harada et al. |
| 5,059,211 A | 10/1991 | Stack et al. |
| 5,095,848 A | 3/1992 | Ikeno |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,171,445 A | 12/1992 | Zepf |
| 5,188,734 A | 2/1993 | Zepf |
| 5,201,314 A | 4/1993 | Bosley et al. |
| 5,219,980 A | 6/1993 | Swidler |
| 5,229,045 A | 7/1993 | Soldani |
| 5,234,457 A | 8/1993 | Andersen |
| 5,242,399 A | 9/1993 | Lau et al. |
| 5,258,020 A | 11/1993 | Froix |
| 5,264,246 A | 11/1993 | Ikeno |
| 5,272,012 A | 12/1993 | Opolski |
| 4,733,665 A | 1/1994 | Palmaz |
| 5,292,516 A | 3/1994 | Viegas et al. |
| 5,298,260 A | 3/1994 | Viegas et al. |
| 5,300,295 A | 4/1994 | Viegas et al. |
| 5,306,286 A | 4/1994 | Stack et al. |
| 5,306,501 A | 4/1994 | Viegas et al. |
| 5,306,786 A | 4/1994 | Moens et al. |
| 5,308,338 A | 5/1994 | Helfrich |
| 5,328,471 A | 7/1994 | Slepian |
| 5,330,768 A | 7/1994 | Park et al. |
| 5,342,621 A | 8/1994 | Eury |
| 5,358,740 A | 10/1994 | Bornside et al. |
| 5,370,684 A | 12/1994 | Vallana et al. |
| 5,378,511 A | 1/1995 | Cardinali et al. |
| 5,380,299 A | 1/1995 | Fearnot et al. |
| 5,417,981 A | 5/1995 | Endo et al. |
| 5,421,955 A | 6/1995 | Lau et al. |
| 5,443,496 A | 8/1995 | Schwartz et al. |
| 5,447,724 A | 9/1995 | Helmus et al. |
| 5,455,040 A | 10/1995 | Marchant |
| 5,458,683 A | 10/1995 | Taylor et al. |
| 5,462,990 A | 10/1995 | Hubbell et al. |
| 5,464,650 A | 11/1995 | Berg et al. |
| 5,485,496 A | 1/1996 | Lee et al. |
| 5,514,154 A | 5/1996 | Lau et al. |
| 5,516,560 A | 5/1996 | Harayama et al. |
| 5,516,881 A | 5/1996 | Lee et al. |
| 5,527,337 A | 6/1996 | Stack et al. |
| 5,537,729 A | 7/1996 | Kolobow |
| 5,538,493 A | 7/1996 | Gerken et al. |
| 5,558,900 A | 9/1996 | Fan et al. |
| 5,569,295 A | 10/1996 | Lam |
| 5,569,463 A | 10/1996 | Helmus et al. |
| 5,578,048 A | 11/1996 | Pasqualucci et al. |
| 5,578,073 A | 11/1996 | Haimovich et al. |
| 5,584,877 A | 12/1996 | Miyake et al. |
| 5,603,721 A | 2/1997 | Lau et al. |
| 5,605,696 A | 2/1997 | Eury et al. |
| 5,607,442 A | 3/1997 | Fischell et al. |
| 5,607,467 A | 3/1997 | Froix |
| 5,609,629 A | 3/1997 | Fearnot et al. |
| 5,610,241 A | 3/1997 | Lee et al. |
| 5,611,775 A | 3/1997 | Machold et al. |
| 5,616,338 A | 4/1997 | Fox, Jr. et al. |
| 5,624,411 A | 4/1997 | Tuch |
| 5,628,730 A | 5/1997 | Shapland et al. |
| 5,628,786 A | 5/1997 | Banas et al. |
| 5,637,113 A | 6/1997 | Tartaglia et al. |
| 5,643,580 A | 7/1997 | Subramaniam |
| 5,644,020 A | 7/1997 | Timmermann et al. |
| 5,649,977 A | 7/1997 | Campbell |
| 5,656,082 A | 8/1997 | Takatsuki et al. |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,687,906 A | 11/1997 | Nakagawa |
| 5,700,286 A | 12/1997 | Tartaglia et al. |
| 5,702,754 A | 12/1997 | Zhong |
| 5,707,385 A | 1/1998 | Williams |
| 5,711,958 A | 1/1998 | Cohn et al. |
| 5,713,949 A | 2/1998 | Jayaraman |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,741,554 A | 4/1998 | Tisone |
| 5,746,998 A | 5/1998 | Torchilin et al. |
| 5,756,553 A | 5/1998 | Iguchi et al. |
| 5,759,205 A | 6/1998 | Valentini |
| 5,766,710 A | 6/1998 | Turnlund et al. |
| 5,769,883 A | 6/1998 | Buscemi et al. |
| 5,772,864 A | 6/1998 | Møller et al. |
| 5,776,184 A | 7/1998 | Tuch |
| 5,783,657 A | 7/1998 | Pavlin et al. |
| 5,788,626 A | 8/1998 | Thompson |
| 5,788,979 A | 8/1998 | Alt et al. |
| 5,800,392 A | 9/1998 | Racchini |
| 5,820,917 A | 10/1998 | Tuch |
| 5,823,996 A | 10/1998 | Sparks |
| 5,824,048 A | 10/1998 | Tuch |
| 5,824,049 A | 10/1998 | Ragheb et al. |
| 5,830,178 A | 11/1998 | Jones et al. |
| 5,833,659 A | 11/1998 | Kranys |
| 5,836,965 A | 11/1998 | Jendersee et al. |
| 5,837,008 A | 11/1998 | Berg et al. |
| 5,837,313 A | 11/1998 | Ding et al. |
| 5,843,172 A | 12/1998 | Yan |
| 5,849,859 A | 12/1998 | Acemoglu |
| 5,851,508 A | 12/1998 | Greff et al. |
| 5,854,376 A | 12/1998 | Higashi |
| 5,855,598 A | 1/1999 | Pinchuk |
| 5,855,600 A | 1/1999 | Alt |
| 5,855,684 A | 1/1999 | Bergmann |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,891,108 A | 4/1999 | Leone et al. |
| 5,891,507 A | 4/1999 | Jayaraman |
| 5,895,407 A | 4/1999 | Jayaraman |
| 5,897,911 A | 4/1999 | Loeffler |

| Patent Number | Kind | Date | Inventor |
|---|---|---|---|
| 5,902,631 | A | 5/1999 | Wang et al. |
| 5,902,875 | A | 5/1999 | Roby et al. |
| 5,905,168 | A | 5/1999 | Dos Santos et al. |
| 5,910,564 | A | 6/1999 | Gruning et al. |
| 5,911,752 | A | 6/1999 | Dustrude et al. |
| 5,914,387 | A | 6/1999 | Roby et al. |
| 5,919,893 | A | 7/1999 | Roby et al. |
| 5,922,393 | A | 7/1999 | Jayaraman |
| 5,925,720 | A | 7/1999 | Kataoka et al. |
| 5,928,279 | A | 7/1999 | Shannon et al. |
| 5,932,299 | A | 8/1999 | Katoot |
| 5,935,135 | A | 8/1999 | Bramfitt et al. |
| 5,948,018 | A | 9/1999 | Dereume et al. |
| 5,955,509 | A | 9/1999 | Webber et al. |
| 5,958,385 | A | 9/1999 | Tondeur et al. |
| 5,962,138 | A | 10/1999 | Kolluri et al. |
| 5,968,091 | A | 10/1999 | Pinchuk et al. |
| 5,971,954 | A | 10/1999 | Conway et al. |
| 5,972,027 | A | 10/1999 | Johnson |
| 5,980,928 | A | 11/1999 | Terry |
| 5,980,972 | A | 11/1999 | Ding |
| 5,984,449 | A | 11/1999 | Tajika et al. |
| 5,997,517 | A | 12/1999 | Whitbourne |
| 6,010,530 | A | 1/2000 | Goicoechea |
| 6,010,573 | A | 1/2000 | Bowlin |
| 6,011,125 | A | 1/2000 | Lohmeijer et al. |
| 6,013,099 | A | 1/2000 | Dinh et al. |
| 6,015,541 | A | 1/2000 | Greff et al. |
| 6,030,371 | A | 2/2000 | Pursley |
| 6,033,582 | A | 3/2000 | Lee et al. |
| 6,034,204 | A | 3/2000 | Mohr et al. |
| 6,042,875 | A | 3/2000 | Ding et al. |
| 6,045,899 | A | 4/2000 | Wang et al. |
| 6,051,576 | A | 4/2000 | Ashton et al. |
| 6,051,648 | A | 4/2000 | Rhee et al. |
| 6,054,553 | A | 4/2000 | Groth et al. |
| 6,056,993 | A | 5/2000 | Leidner et al. |
| 6,059,714 | A | 5/2000 | Armini et al. |
| 6,060,451 | A | 5/2000 | DiMaio et al. |
| 6,060,518 | A | 5/2000 | Kabanov et al. |
| 6,068,202 | A | 5/2000 | Hynes et al. |
| 6,071,305 | A | 6/2000 | Brown et al. |
| 6,080,488 | A | 6/2000 | Hostettler et al. |
| 6,096,070 | A | 8/2000 | Ragheb et al. |
| 6,099,562 | A | 8/2000 | Ding et al. |
| 6,106,889 | A | 8/2000 | Beavers et al. |
| 6,110,188 | A | 8/2000 | Narciso, Jr. |
| 6,110,483 | A | 8/2000 | Whitbourne et al. |
| 6,113,629 | A | 9/2000 | Ken |
| 6,120,491 | A | 9/2000 | Kohn et al. |
| 6,120,536 | A | 9/2000 | Ding et al. |
| 6,120,788 | A | 9/2000 | Barrows |
| 6,120,847 | A | 9/2000 | Yang et al. |
| 6,120,904 | A | 9/2000 | Hostettler et al. |
| 6,121,027 | A | 9/2000 | Clapper et al. |
| 6,126,686 | A | 10/2000 | Badylak et al. |
| 6,129,755 | A | 10/2000 | Mathis et al. |
| 6,129,761 | A | 10/2000 | Hubbell |
| 6,136,333 | A | 10/2000 | Cohn et al. |
| 6,140,127 | A | 10/2000 | Sprague |
| 6,140,431 | A | 10/2000 | Kinker et al. |
| 6,143,354 | A | 11/2000 | Koulik et al. |
| 6,143,370 | A | 11/2000 | Panagiotou et al. |
| 6,153,252 | A | 11/2000 | Hossainy et al. |
| 6,156,373 | A | 12/2000 | Zhong et al. |
| 6,159,978 | A | 12/2000 | Myers et al. |
| 6,165,212 | A | 12/2000 | Dereume et al. |
| 6,165,267 | A | 12/2000 | Torczynski |
| 6,171,334 | B1 | 1/2001 | Cox |
| 6,172,167 | B1 | 1/2001 | Stapert et al. |
| 6,174,329 | B1 | 1/2001 | Callol et al. |
| 6,177,523 | B1 | 1/2001 | Reich et al. |
| 6,180,632 | B1 | 1/2001 | Myers et al. |
| 6,194,034 | B1 | 2/2001 | Nishi et al. |
| 6,197,013 | B1 | 3/2001 | Reed et al. |
| 6,203,551 | B1 | 3/2001 | Wu |
| 6,203,569 | B1 | 3/2001 | Wijay |
| 6,206,915 | B1 | 3/2001 | Fagan et al. |
| 6,211,249 | B1 | 4/2001 | Cohn et al. |
| 6,214,115 | B1 | 4/2001 | Taylor et al. |
| 6,214,901 | B1 | 4/2001 | Chudzik et al. |
| 6,228,072 | B1 | 5/2001 | Omaleki et al. |
| 6,231,600 | B1 | 5/2001 | Zhong |
| 6,235,340 | B1 | 5/2001 | Lee et al. |
| 6,240,616 | B1 | 6/2001 | Yan |
| 6,244,575 | B1 | 6/2001 | Vaartstra et al. |
| 6,245,099 | B1 | 6/2001 | Edwin et al. |
| 6,245,753 | B1 | 6/2001 | Byun et al. |
| 6,245,760 | B1 | 6/2001 | He et al. |
| 6,248,129 | B1 | 6/2001 | Froix |
| 6,248,398 | B1 | 6/2001 | Talieh et al. |
| 6,251,136 | B1 | 6/2001 | Guruwaiya et al. |
| 6,254,632 | B1 | 7/2001 | Wu et al. |
| 6,258,121 | B1 | 7/2001 | Yang et al. |
| 6,258,371 | B1 | 7/2001 | Koulik et al. |
| 6,261,320 | B1 | 7/2001 | Tam et al. |
| 6,262,034 | B1 | 7/2001 | Mathiowitz et al. |
| 6,270,504 | B1 | 8/2001 | Lorentzen Cornelius et al. |
| 6,270,788 | B1 | 8/2001 | Koulik et al. |
| 6,273,878 | B1 | 8/2001 | Muni |
| 6,273,908 | B1 | 8/2001 | Ndondo-Lay |
| 6,273,910 | B1 | 8/2001 | Limon |
| 6,273,913 | B1 | 8/2001 | Wright et al. |
| 6,277,449 | B1 | 8/2001 | Kolluri et al. |
| 6,279,368 | B1 | 8/2001 | Escano et al. |
| 6,283,947 | B1 | 9/2001 | Mirzaee |
| 6,283,949 | B1 | 9/2001 | Roorda |
| 6,284,305 | B1 | 9/2001 | Ding et al. |
| 6,287,249 | B1 | 9/2001 | Tam et al. |
| 6,287,628 | B1 | 9/2001 | Hossainy et al. |
| 6,299,604 | B1 | 10/2001 | Ragheb et al. |
| 6,306,165 | B1 | 10/2001 | Patnaik et al. |
| 6,306,176 | B1 | 10/2001 | Whitbourne |
| 6,322,847 | B1 | 11/2001 | Zhong et al. |
| 6,331,191 | B1 | 12/2001 | Chobotov |
| 6,331,313 | B1 | 12/2001 | Wong et al. |
| 6,335,029 | B1 | 1/2002 | Kamath et al. |
| 6,344,035 | B1 | 2/2002 | Chudzik et al. |
| 6,346,110 | B2 | 2/2002 | Wu |
| 6,358,556 | B1 | 3/2002 | Ding et al. |
| 6,358,567 | B2 | 3/2002 | Pham et al. |
| 6,364,903 | B2 | 4/2002 | Tseng et al. |
| 6,368,658 | B1 | 4/2002 | Schwarz et al. |
| 6,372,283 | B1 | 4/2002 | Shim et al. |
| 6,379,381 | B1 | 4/2002 | Hossainy et al. |
| 6,383,215 | B1 | 5/2002 | Sass |
| 6,387,118 | B1 | 5/2002 | Hanson |
| 6,387,379 | B1 | 5/2002 | Goldberg et al. |
| 6,395,326 | B1 | 5/2002 | Castro et al. |
| 6,407,009 | B1 | 6/2002 | You et al. |
| 6,416,543 | B1 | 7/2002 | Hilaire et al. |
| 6,419,692 | B1 | 7/2002 | Yang et al. |
| 6,435,798 | B1 | 8/2002 | Satoh |
| 6,440,221 | B2 | 8/2002 | Shamouilian et al. |
| 6,451,373 | B1 | 9/2002 | Hossainy et al. |
| 6,475,779 | B2 | 11/2002 | Mathiowitz et al. |
| 6,482,834 | B2 | 11/2002 | Spada et al. |
| 6,494,862 | B1 | 12/2002 | Ray et al. |
| 6,503,538 | B1 | 1/2003 | Chu et al. |
| 6,503,556 | B2 | 1/2003 | Harish et al. |
| 6,503,954 | B1 | 1/2003 | Bhat et al. |
| 6,506,437 | B1 | 1/2003 | Harish et al. |
| 6,517,534 | B1 | 2/2003 | McGovern et al. |
| 6,517,889 | B1 | 2/2003 | Jayaraman |
| 6,521,284 | B1 | 2/2003 | Parsons et al. |
| 6,524,347 | B1 | 2/2003 | Myers et al. |
| 6,527,801 | B1 | 3/2003 | Dutta |
| 6,527,863 | B1 | 3/2003 | Pacetti et al. |
| 6,528,526 | B1 | 3/2003 | Myers et al. |
| 6,530,950 | B1 | 3/2003 | Alvarado et al. |
| 6,530,951 | B1 | 3/2003 | Bates et al. |
| 6,534,112 | B1 | 3/2003 | Bouchier et al. |
| 6,540,776 | B2 | 4/2003 | Sanders Millare et al. |
| 6,544,223 | B1 | 4/2003 | Kokish |
| 6,544,543 | B1 | 4/2003 | Mandrusov et al. |
| 6,544,582 | B1 | 4/2003 | Yoe |
| 6,555,157 | B1 | 4/2003 | Hossainy |
| 6,558,733 | B1 | 5/2003 | Hossainy et al. |

| | | |
|---|---|---|
| 6,562,136 B1 | 5/2003 | Chappa et al. |
| 6,565,659 B1 | 5/2003 | Pacetti et al. |
| 6,572,644 B1 | 6/2003 | Moein |
| 6,572,651 B1 | 6/2003 | De Scheerder et al. |
| 6,575,933 B1 | 6/2003 | Wittenberger et al. |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,610,087 B1 | 8/2003 | Zarbatany et al. |
| 6,613,432 B2 | 9/2003 | Zamora et al. |
| 6,616,765 B1 | 9/2003 | Castro et al. |
| 6,620,617 B2 | 9/2003 | Mathiowitz et al. |
| 6,623,448 B2 | 9/2003 | Slater |
| 6,625,486 B2 | 9/2003 | Lundkvist et al. |
| 6,641,611 B2 | 11/2003 | Jayaraman |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,676,700 B1 | 1/2004 | Jacobs et al. |
| 6,682,771 B2 | 1/2004 | Zhong et al. |
| 6,689,099 B2 | 2/2004 | Mirzaee |
| 6,689,350 B2 | 2/2004 | Uhrich |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,723,373 B1 | 4/2004 | Narayanan et al. |
| 6,730,064 B2 | 5/2004 | Ragheb et al. |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,776,796 B2 | 8/2004 | Falotico et al. |
| 6,780,424 B2 | 8/2004 | Claude |
| 6,790,228 B2 | 9/2004 | Hossainy et al. |
| 6,818,063 B1 | 11/2004 | Kerrigan |
| 6,824,559 B2 | 11/2004 | Michal |
| 6,860,946 B2 | 3/2005 | Hossainy et al. |
| 6,887,510 B2 | 5/2005 | Villareal |
| 6,890,583 B2 | 5/2005 | Chudzik et al. |
| 6,955,723 B2 | 10/2005 | Pacetti et al. |
| 2001/0007083 A1 | 7/2001 | Roorda |
| 2001/0029351 A1 | 10/2001 | Falotico et al. |
| 2001/0037145 A1 | 11/2001 | Guruwaiya et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0050220 A1 | 5/2002 | Schueller et al. |
| 2002/0051730 A1 | 5/2002 | Bodnar et al. |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0088307 A1 | 5/2003 | Shulze et al. |
| 2003/0097088 A1 | 5/2003 | Pacetti |
| 2003/0097173 A1 | 5/2003 | Dutta |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0158517 A1 | 8/2003 | Kokish |
| 2003/0190406 A1 | 10/2003 | Hossainy et al. |
| 2003/0211230 A1 | 11/2003 | Pacetti et al. |
| 2003/0215564 A1 | 11/2003 | Heller et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0191405 A1 | 9/2004 | Kerrigan |
| 2004/0213893 A1 | 10/2004 | Boulais |
| 2005/0069630 A1 | 3/2005 | Fox et al. |
| 2005/0074544 A1 | 4/2005 | Pacetti et al. |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 627 226 | 12/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 875 218 | 11/1998 |
| EP | 0 879 595 | 11/1998 |
| EP | 0 897 701 | 2/1999 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 05009726 A | 1/1993 |
| JP | 11299901 | 11/1999 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |

| WO | WO 90/01969 | 3/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/23228 | 6/1998 |
| WO | WO 98/32398 | 7/1998 |
| WO | WO 98/36784 | 8/1998 |
| WO | WO 99/01118 | 1/1999 |
| WO | WO 99/16386 | 4/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/00112 | 1/2001 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

U.S. Appl. No. 09/894,293, filed Jun. 27, 2001, Roorda et al.
U.S. Appl. No. 09/997,390, filed Nov. 30, 2001, Pacetti.
U.S. Appl. No. 10/040,538, filed Dec. 28, 2001, Pacetti et al.
U.S. Appl. No. 10/255,913, filed Sep. 26, 2002, Tang et al.
U.S. Appl. No. 10/262,161, filed Sep. 30, 2002, Pacetti.
U.S. Appl. No. 10/266,479, filed Oct. 8, 2002, Hossainy.
U.S. Appl. No. 10/304,669, filed Nov. 25, 2002, Madriaga et al.
U.S. Appl. No. 10/319,042, filed Dec. 12, 2002, Van Sciver et al.
U.S. Appl. No. 10/330,412, filed Dec. 27, 2002, Hossainy et al.
U.S. Appl. No. 10/376,027, filed Feb. 26, 2003, Kokish et al.
U.S. Appl. No. 10/438,378, filed May 15, 2003, Esbeck et al.
U.S. Appl. No. 10/660,853, filed Sep. 12, 2003, Pacetti et al.
U.S. Appl. No. 10/729,551, filed Dec. 5, 2003, Pacetti.
U.S. Appl. No. 10/729,728, filed Dec. 5, 2003, Pacetti.
U.S. Appl. No. 10/750,312, filed Dec. 30, 2003, Desnoyer et al.
U.S. Appl. No. 10/805,047, filed Mar. 18, 2004, Yip et al.
U.S. Appl. No. 10/813,845, filed Mar. 30, 2004, Pacetti.
U.S. Appl. No. 10/817,642, filed Apr. 2, 2004, Kerrigan.
U.S. Appl. No. 11/193,849, filed Jul. 28, 2005, Harold et al.
Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Coating Techniques, *Air Knife Coating*, http://www.ferron-magnetic.co.uk/coatings/airknife.htm, 1 page, printed Jul. 1, 2003.
Coating Techniques, *Gap Coating*, http://www.ferron-magnetic.co.uk/coatings/knife.htm, 1 page, printed Jul. 1, 2003.
Coating Techniques, *Gravure Coating*, http://www.ferron-magnetic.co.uk/coatings/gravure.htm, 2 pages, printed Jul. 1, 2003.
Coating Techniques, *Reverse Roll Coating*, http://www.ferron-magnetic.co.uk/coatings/revroll.htm, 2 pages, printed Jul. 1, 2003.
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Forrester et al., *A Paradigm for Restenosis Based on Cell Biology: Clues for the Development of New Preventive Therapies*; J. Am. Coll. Cardio. 1991; 17:758-769.
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Illbruck Sealant Systems, *Application: Window and Perimeter Silicone*, http://www.willseal.com/usa/produktuebersicht/dichtstoffe/perwindow/verlege_anleitung . . . , printed Nov. 29, 2004 (3 pages).
Inoue et al., *An AB block copolymer of oligo(methyl methacrylate) and poly(acrylic acid) for micellar delivery of hydrophobic drugs*, Journal of Controlled Release 51:221-229 (1998).
*International Search Report and Written Opinion*, dated Mar. 1, 2005 for PCT Application No. PCT/US2004/031185, filed Sep. 22, 2004 (14 pages).
Kataoka et al., *Block copolymer micelles as vehicles for drug delivery*, Journal of Controlled Release 24:119-132 (1993).
Kim, *Solid State Sintering*, AMSE 604 Solid State Reactions and Sintering, Electroceramic laboratory in Dept. of Materials Science & Engineering, POSTECH, Pohang University of Science and Technology (20 pages).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials For Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*; Chemical Abstract 125:212307 (1996).

van Beusekom et al., *Coronary stent coatings*, Coronary Artery Disease 5(7):590-596 (Jul. 1994).

Van Iseghem, *Important Concepts on Coating Plastics From a Formulator's Perspective*, Modern Paint and Coatings, pp. 30-38 (Feb. 1998).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

METHOD OF USING A MANDREL TO COAT A STENT

CROSS REFERENCE

This is a divisional application of U.S. Ser. No. 10/678,979, which was filed on Oct. 2, 2003 now U.S. Pat. No. 6,955,723 as a divisional application of U.S. Ser. No. 09/894,248, filed on Jun. 27, 2001 now U.S. Pat. No. 6,695,920.

BACKGROUND OF THE INVENTION

1. Field of the Invention

This invention relates to a method of applying a coating to a stent supported by a mandrel.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway.

Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Figures 1, 2A:
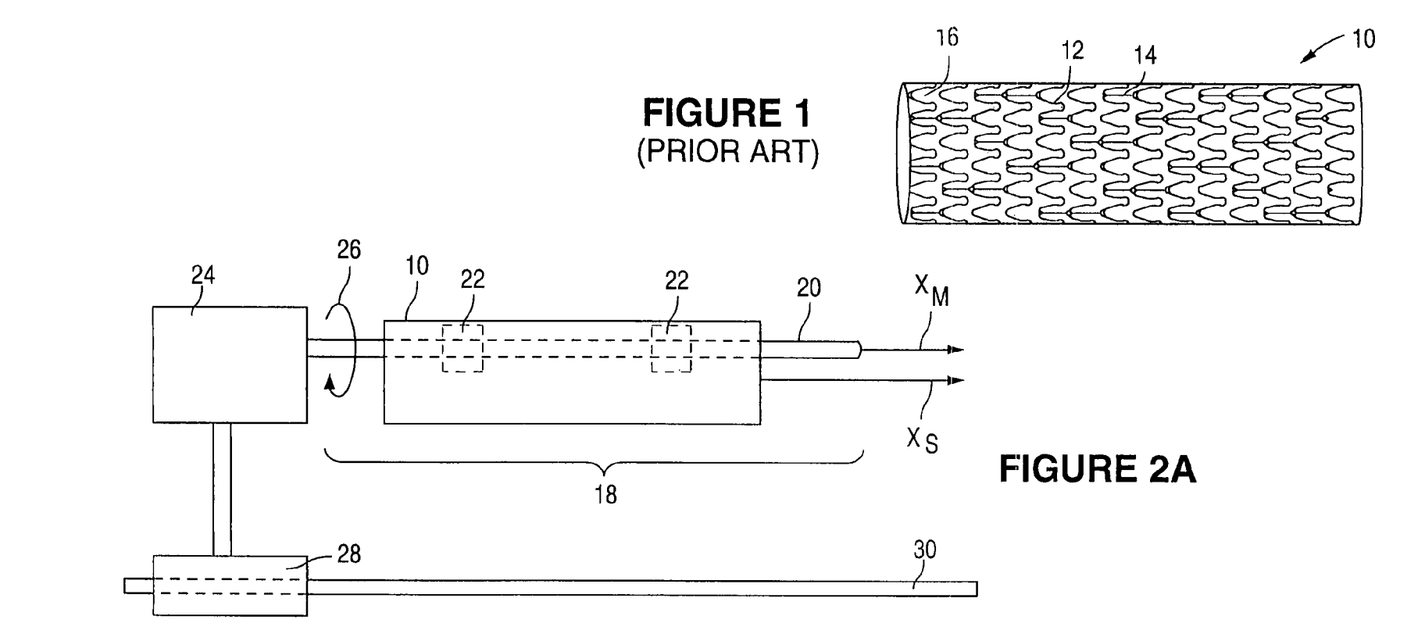
FIG. 1 illustrates a conventional stent.
FIG. 2A illustrates a mounting assembly for supporting a stent.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts.

Thus, it is desirable to minimize the interface between the stent and the apparatus supporting the stent during the coating process to minimize coating defects. Accordingly, the present invention provides for a device for supporting a stent during the coating application process. The invention also provides for a method of coating the stent supported by the device.

SUMMARY OF THE INVENTION

The present invention provides a method of coating a stent. The method includes positioning a stent on a gear. The gear is supported by a mandrel. The method further includes rotating the mandrel to cause the gear to provide rotational motion to the stent. The method additionally includes applying a coating material to the stent.

Another aspect of the invention provides a method of coating a stent including positioning a stent on a gear. The method further includes rotating the gear to provide rotational motion to the stent. The method additionally includes applying a coating material to the stent.

A further aspect of the invention provides a method of coating a stent that includes positioning a stent on a mandrel. The mandrel includes a body extending into the stent that includes a textured or roughened surface area for the stent to rest thereon. The method further includes applying a coating material to the stent.

An additional aspect of the invention provides a method of coating a stent including adjusting a position of a gear along a length of a mandrel. The method further includes positioning a stent on the gear. The mandrel is rotated to rotate the stent. The method further includes applying a coating material to the stent.

DETAILED DESCRIPTION

Embodiments of the Mounting Assembly

Various types of coating defects can arise due to permanent contact points between a stent and its supporting apparatus. The present invention minimizes or eliminates such coating defects by having no permanent contact points between a stent and its supporting apparatus during the coating process.

Referring to FIG. 2A, a mounting assembly 18 for supporting stent 10 is illustrated to include a rod or mandrel 20 and gear members 22. Mandrel 20 can connect to a motor 24, which provides rotational motion to mandrel 20, as depicted by arrow 26, during the coating process. Another motor 28 can also be provided for moving mandrel 20 and thus stent 10 in a linear direction, back and forth, along a rail 30.

Mandrel 20 is illustrated as having two regions with a larger diameter. The two regions can be gear members 22 for applying a torque to stent 10. In commercially useful embodiments, any number of gear members 22 can be used to adequately support stent 10, and the embodiments of the present invention should not be limited to a mandrel 20 having merely two gear members 22 as illustrated in the Figures. Gear members 22 should be sized larger than the outer diameter of mandrel 20 so as to prevent mandrel 20 from being in contact with the inner surface of stent 10. Additionally, gear members 22 should be sized smaller than the inner diameter of stent 10 so as to provide for minimum contact between gear members 22 and the inner surface of stent 10. Providing gear members 22 of small diameter, as compared to the inner diameter of stent 10 offsets the gear member 22 rotation axis $x_M$, from the axis about which stent 10 rotates—axis $X_s$ being positioned longitudinally through the center of stent 10. Exemplary specifications that can be employed with stent 10 having a length of about 18 mm and an inner diameter of about 1.8 mm include:

| Component | Length (mm) | Diameter (mm) |
|---|---|---|
| Mandrel | 40 | 0.38 |
| Gear member | 1.5 | 0.9 |

Figure 2B:
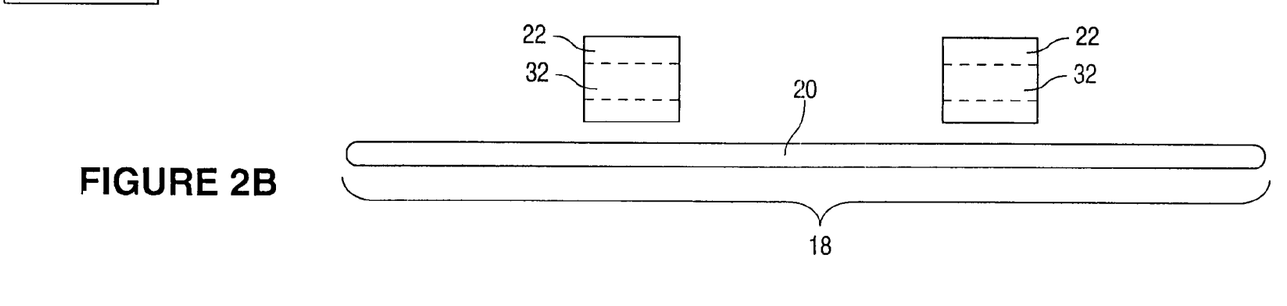
FIG. 2B illustrates an expanded view of the mounting assembly in accordance with one embodiment of the present invention.

In accordance with one embodiment, gear members 22 can be permanently affixed to mandrel 20. Alternatively, gear members 22 can be adjustably coupled to mandrel 20. As illustrated in FIG. 2B, in such an embodiment, gear members 22 can include bores 32 for receiving mandrel 20. Bores 32 can extend completely through gear members 22. By way of example, mandrel 20 and bores 32 can be threaded such that the clockwise or counterclockwise rotation of gear members 22 would allow the user to adjust the location of gear members 22 along mandrel 20 to most suitably support stent 10.

Figure 3A:
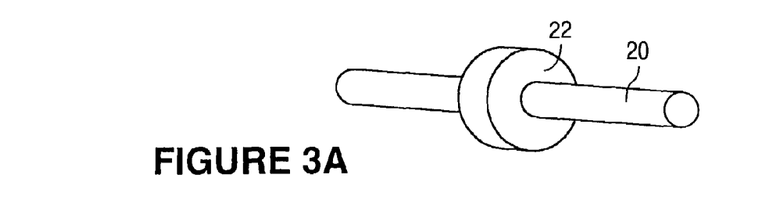
FIGS. 3A and 3B are perspective views of the gear members of the mounting assembly in accordance with various embodiments of the present invention.
Figure 3B:
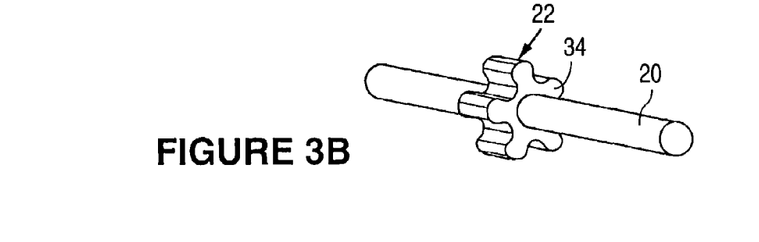

The body of gear members 22 can be of any suitable shape. For example, gear members 22 can be without teeth, as illustrated in FIG. 3A, or can include teeth 34, as illustrated in FIG. 3B. The number, size, and spacing of teeth 34 can be selected to coordinate with the type of stent 10 employed. In addition, the outer surface of gear members 22 can be textured or roughened for creating suitable friction against the inner surface of stent 10. However, the texture of the outer surface of gear members 22 should not be so rough or jagged as to cause any damage to the inner surface of stent 10.

Figure 4:
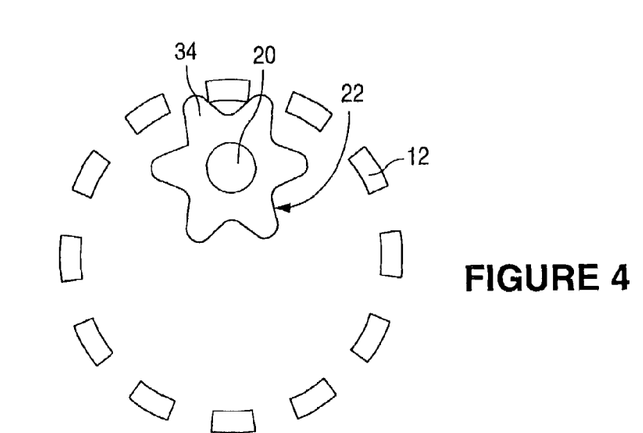
FIG. 4 is an end view of the interface between the mounting assembly and the stent in accordance with one embodiment of the present invention.

FIG. 4 illustrates the contact interface between gear member 22 and stent 10. Gear member 22 is in minimum contact with stent 10. Moreover, the revolution of stent 10 about gear member 22 allows the contact points between stent 10 and mounting assembly 18 to be transient rather than permanent, thereby preventing the coating material from flowing, wicking, collecting, and solidifying at or between gear member 22 and stent 10.

Figure 5:
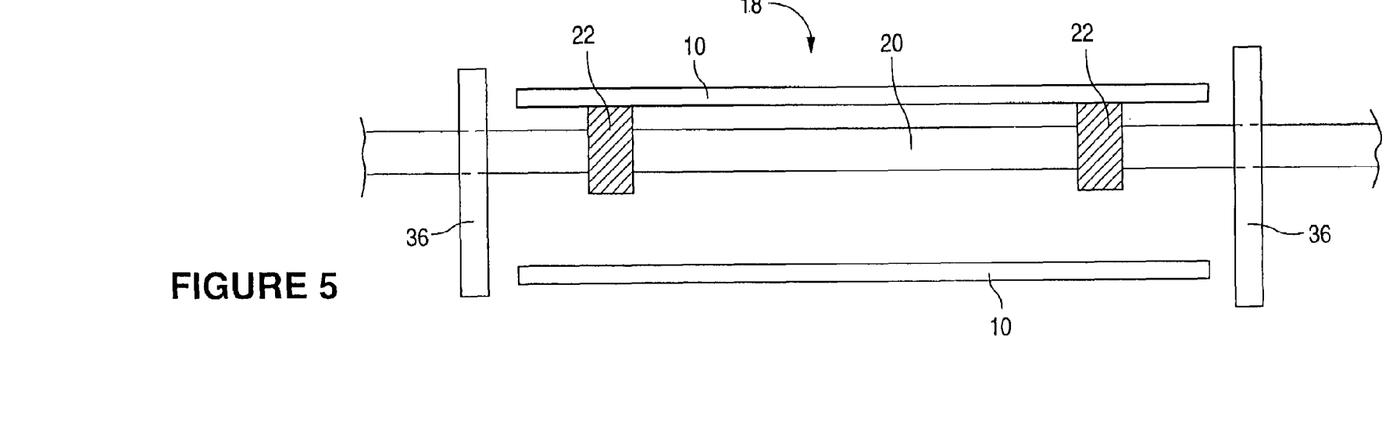
FIG. 5 is a cross-sectional view of the interface between the mounting assembly and the stent in accordance with one embodiment of the present invention.

FIG. 5 is a cross-sectional view of the interface between stent 10 and mounting assembly 18. In one embodiment, optional barrier members 36 can be employed so as to prevent stent 10 from sliding off of mounting assembly 18. Barrier members 36 can be spaced at a distance from stent 10 so as to prevent collection of coating material between barrier members 36 and the ends of stent 10. At least one barrier member 36 should be disengagable from mandrel 20 so as to allow mounting and dismounting of stent 10.

Coating a Stent Using the Mounting Assembly

The following method of application is being provided by way of illustration and is not intended to limit the embodiments of mounting assembly 18 of the present invention. A spray apparatus, such as EFD 780S spray device with VALVEMATE 7040 control system (manufactured by EFD Inc., East Providence, R.I.), can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition.

During the application of the composition, mandrel 20 can be rotated about its own central longitudinal axis. Rotation of mandrel 20 can be from about 10 rpm to about 300 rpm, more narrowly from about 40 rpm to about 240 rpm. By way of example, mandrel 20 can rotate at about 100 rpm. Mandrel 20 can also be moved in a linear direction along the same axis. Mandrel 20 can be moved at about 1 mm/second to about 6 mm/second, for example about 3 mm/second, or for a minimum of at least two passes (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/cm$^2$ (of stent surface) to about 40 micrograms/cm$^2$, for example less than about 2 micrograms/cm$^2$ per 5-second spray.

Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2-4 hours) or by the application of warm air. The application of warm air between each repetition prevents coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer in a single application can, however, cause coating defects.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

In accordance with one embodiment, the composition can include a solvent and a polymer dissolved in the solvent. The composition can also include active agents, radiopaque elements, or radioactive isotopes. Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a stent, comprising:
    positioning a stent on a gear, the gear being supported by a mandrel and having a diameter greater than a diameter of the mandrel;
    rotating the mandrel to cause the gear to provide rotational motion to the stent; and applying a coating material to the stent;
    wherein an outer surface of the mandrel does not make contact with an inner surface of the stent; and
    wherein the gear has a shape or diameter configured so that a contact area between the gear and stent changes as the stent rotates.

2. The method of claim 1, wherein a second gear is integrated with the mandrel, the second gear being configured to allow the stent to rest thereon.

3. The method of claim 1, wherein the gear has teeth.

4. The method of claim 1, wherein the gear is adjustably integrated with the mandrel.

5. The method of claim 1, wherein the gear is star-shaped.

6. The method of claim 1, wherein the gear has a textured or roughened surface.

7. The method of claim 1, wherein the stent comprises struts and gaps disposed between the struts, wherein the gear has teeth sized to fit into the gaps of the stent.

8. A method of coating a stent, comprising:
    positioning a stent on a gear, the gear being supported by a mandrel and having a diameter greater than a diameter of the mandrel;
    rotating the mandrel to cause the gear to provide rotational motion to the stent; and
    applying a coating material to the stent;
    wherein applying the coating material comprises spraying a composition including a polymer added to a solvent, and optionally an active agent added thereto, onto the stent;
    wherein the gear is configured to allow the stent to rest on the gear so as to form a contact area between an outer surface of the gear and an inner surface of the stent, and wherein a shape or diameter of the gear is configured so that the contact area changes location as the stent is rotated.

9. The method of claim 8, wherein the composition is sprayed onto the stent in a downward direction.

10. The method of claim 8, wherein a second gear is integrated with the mandrel, the second gear being configured to allow the stent to rest thereon.

11. The method of claim 8, wherein the gear is substantially circular along an outer circumference of the gear.

12. The method of claim 8, wherein the gear has teeth.

13. The method of claim 8, wherein the gear is adjustably integrated with the mandrel.

14. The method of claim 8, wherein the gear is star-shaped.

15. The method of claim 8, wherein the gear has a textured or roughened surface.

16. The method of claim 8, wherein the stent comprises struts and gaps disposed between the struts, wherein the gear has teeth sized to fit into the gaps of the stent.

17. A method of coating a stent, comprising:
    positioning a stent on a gear, the gear being supported by a mandrel and having a diameter greater than a diameter of the mandrel;
    rotating the mandrel to cause the gear to provide rotational motion to the stent; applying a coating material to the stent; and
    moving the stent in a linear direction along a longitudinal axis of the stent during the application of the coating material;
    wherein the stent comprises struts and gaps disposed between the struts, wherein the gear has teeth sized to fit into the gaps of the stent.

18. The method of claim 17, wherein the gear is configured to allow the stent to rest on the gear so as to form a contact area between an outer surface of the gear and an inner surface of the stent, and wherein a shape or diameter of the gear is configured so that the contact area changes location as the stent is rotated.

19. The method of claim 17, wherein a second gear is integrated with the mandrel, the second gear being configured to allow the stent to rest thereon.

20. The method of claim 17, wherein the gear is substantially circular along an outer circumference of the gear.

21. The method of claim 17, wherein the gear has teeth.

22. The method of claim 17, wherein the gear is adjustably integrated with the mandrel.

23. The method of claim 17, wherein the gear is star-shaped.

24. The method of claim 17, wherein the gear has a textured or roughened surface.

25. A method of coating a stent, comprising:
    adjusting a position of a gear along a length of a mandrel, the gear having teeth;
    positioning a stent on the gear;
    rotating the mandrel to rotate the stent; and
    applying a coating material to the stent;
    wherein the gear has a threaded bore to allow the gear to be adjusted along the length of the mandrel.

26. The method of claim 25, wherein the gear is positioned to support an inner surface of the stent as the coating material is applied to the stent.

27. The method of claim 25, wherein the gear is configured to allow the stent to rest on the gear so as to form a contact area between an outer surface of the gear and an inner surface of the stent, and wherein a shape or diameter of the gear is configured so that the contact area changes location as the stent is rotated.

28. The method of claim 25, wherein a second gear is integrated with the mandrel, the second gear being configured to allow the stent to rest thereon.

29. The method of claim 25, wherein the gear is substantially circular along an outer circumference of the gear.

30. The method of claim 25, wherein the gear is star-shaped.

31. The method of claim 25, wherein the gear has a textured or roughened surface.

32. The method of claim 25, wherein the stent comprises struts and gaps disposed between the struts, wherein the gear has teeth sized to fit into the gaps of the stent.

33. A method of coating a stent, comprising:
    positioning a stent on a gear;
    rotating a mandrel to cause the gear to provide rotational motion to the stent; and
    applying a coating material to the rotating stent;
    wherein the gear has a rotation axis and the rotating step is such that the stent rotates about an axis offset from the rotation axis.

34. The method of claim 33, wherein the gear is configured to allow the stent to rest on the gear so as to form a contact area between an outer surface of the gear and an inner surface of the stent, and wherein a shape or diameter of the gear is configured so that the contact area changes location as the stent is rotated.

35. The method of claim 33, wherein a second gear is integrated with the mandrel, the second gear being configured to allow the stent to rest thereon.

36. The method of claim 33, wherein the gear is substantially circular along an outer circumference of the gear.

37. The method of claim 33, wherein the gear has teeth.

38. The method of claim 33, wherein the gear is adjustably integrated with the mandrel.

39. The method of claim 33, wherein the gear is star-shaped.

* * * * *